United States Patent
Friedman

(10) Patent No.: US 7,867,545 B2
(45) Date of Patent: Jan. 11, 2011

(54) HOMOGENOUS GRANULAR SOLID MATRIX CONTAINING VEGETABLE PROTEIN

(75) Inventor: Doron I. Friedman, Karme Yosef (IL)

(73) Assignee: J.P.M.E.D. Ltd., Karme-Yosef (IL)

( * ) Notice: Subject to any disclaimer, the term of this patent is extended or adjusted under 35 U.S.C. 154(b) by 974 days.

(21) Appl. No.: 11/685,124

(22) Filed: Mar. 12, 2007

(65) Prior Publication Data

US 2008/0008756 A1    Jan. 10, 2008

Related U.S. Application Data

(63) Continuation-in-part of application No. 10/203,178, filed as application No. PCT/IL01/00128 on Feb. 8, 2001, now abandoned.

(30) Foreign Application Priority Data

Feb. 23, 2000    (IL)    ................................ 134701

(51) Int. Cl.
    *A61K 47/46*    (2006.01)
(52) U.S. Cl. ................. 426/656; 426/634; 426/93; 426/96; 426/98; 514/783; 424/484
(58) Field of Classification Search ................. 426/656, 426/634, 93, 96, 98; 424/484; 514/783
See application file for complete search history.

(56) References Cited

U.S. PATENT DOCUMENTS

| | | |
|---|---|---|
| 3,303,182 A | 2/1967 | Sakai et al. |
| 3,914,443 A | 10/1975 | Sakita et al. |
| 4,404,228 A | 9/1983 | Cloosterman et al. |
| 4,610,875 A | 9/1986 | Panoz et al. |
| 4,758,427 A | 7/1988 | Leeson |
| 4,880,623 A | 11/1989 | Piergiorgio et al. |
| 5,382,535 A | 1/1995 | Malhi et al. |
| 5,491,154 A | 2/1996 | Ciceri et al. |
| 5,558,880 A | 9/1996 | Gole et al. |
| 5,684,093 A | 11/1997 | Tack et al. |
| 5,725,899 A | 3/1998 | Cole et al. |
| 5,728,403 A | 3/1998 | Mauger et al. |
| 5,776,495 A | 7/1998 | Duclos et al. |
| 5,785,984 A * | 7/1998 | Kurihara et al. ............. 424/439 |
| 5,840,340 A | 11/1998 | Milstein et al. |
| 5,904,936 A | 5/1999 | Huille et al. |
| 5,904,937 A | 5/1999 | Augello et al. |
| 5,972,373 A | 10/1999 | Vajima et al. |
| 5,972,387 A | 10/1999 | Milstein et al. |
| 6,004,973 A | 12/1999 | Guitard et al. |

FOREIGN PATENT DOCUMENTS

| | | |
|---|---|---|
| DE | 43442124 | 6/1995 |
| DE | 4424085 | 1/1996 |
| JP | 05320057 | 12/1993 |

* cited by examiner

*Primary Examiner*—Anthony Weier
(74) *Attorney, Agent, or Firm*—Townsend and Townsend and Crew LLP

(57) ABSTRACT

The present invention relates to a homogeneous solid matrix composition containing vegetable proteins, lecithin and at least one ingestible bioactive compound which is at least partially insoluble in an aqueous medium.

20 Claims, 2 Drawing Sheets

HOMOGENOUS GRANULAR SOLID MATRIX CONTAINING VEGETABLE PROTEIN

CROSS-REFERENCES TO RELATED APPLICATIONS

The present specification is a continuation-in-part of U.S. application Ser. No. 10/203,178, filed on Aug. 5, 2002, which is a national phase application under 35 U.S.C. §371 of PCT/IL01/00128, filed Feb. 8, 2001, which claims the benefit of IL Application No. 134,701, filed Feb. 23, 2000. The entire disclosures of each of which are hereby incorporated by reference.

BACKGROUND OF THE INVENTION

The present invention relates to a homogeneous solid matrix composition containing vegetable proteins, lecithin and at least one ingestible bioactive compound which is at least partially insoluble in an aqueous medium. The term, "at least partially insoluble in an aqueous medium", as used herein, is intended to denote a compound having low or poor water solubility as well as compounds which are water insoluble due to the presence of at least a hydrophobic moiety in the compound or, the hydrophobicity of the compound as a whole.

The bioactive compound is homogeneously embedded in an amorphous, non-crystalline form in the matrix for achieving the advantages of enhanced dissolution and biological availability of said ingestible, bioactive compounds to be administered to mammals, as well as the advantage of masking the bitter taste of ingestible substances.

This invention has been developed to provide a solution for an unmet therapeutic and nutraceutic need, that of low biological availability of: drugs, phytomedicines, phytonutrients, vitamins and nutraceutical or food supplements, especially herbal extracts comprising variable levels of assembly of hydrophobic constituents, which do not mix or disperse well enough in the gastrointestinal physiological fluids. These have low dissolution, low oral bioavailability and large inter-individual availability variations, all of which are obstacles for maximizing their potential.

Since most bitter tasting compounds are poorly water soluble or at least have a hydrophobic moiety, this invention has been developed to provide a solution for an unmet therapeutic and nutraceutic need, i.e., that of finding a vehicle for administration of such bitter tasting drugs and nutrients.

The granules of the current invention are made of vegetable proteins which are solidified into granules upon a denaturing heat process and which then are non-soluble in water and are broken down upon digestion by proteolytic intestinal enzymes.

BRIEF SUMMARY OF THE INVENTION

According to the present invention, there is now provided a homogeneous, granular, solid matrix composition that is substantially insoluble in aqueous medium, and substantially insoluble for at least two hours in gastric juices, and which solid matrix completely disintegrates in the presence of digestive proteolytic enzymes or intestinal juices said solid matrix comprising: a) at least 10% w/w vegetable proteins; b) lecithin; c) and at least one ingestible bioactive compound, which compound is at least partially insoluble in an aqueous medium and is dispersed or solubilized in said granular solid matrix.

In preferred embodiments of the present invention said solid granules do not disintegrate or substantially loose their shape within two hours in simulated gastric fluids, and wherein said solid matrix substantially disintegrates within six hours in simulated intestinal fluids comprising pancreatic enzymes.

Preferably said bioactive agent which is at least partially insoluble in an aqueous medium is embedded in a substantially molecular or uniform non-crystalline dispersion.

In preferred embodiments of the present invention, the ratio of vegetable protein to the combined amounts of lecithin and ingestible bioactive compound is between about 40:1 and 1:4.

Preferably the ratio of vegetable protein to the combined amounts of lecithin and ingestible bioactive compound is between about 10:1 and 1:1.

In especially preferred embodiments of the present invention said ingestible bioactive compound has a water solubility of less than 10 mg/ml at 25° C.

In preferred embodiments of the present invention, said vegetable proteins are concentrated and isolated proteins selected from the group consisting of: corn, potatoes, wheat, peanuts, beans, rice, sesame, barley, sunflower, canola and rapeseed.

Preferably said ingestible bioactive compound is selected from the group consisting of: a drug, a nutrient, a vitamin, a food supplement, an enzyme, a coenzyme, an oil, omega 3, omega 6, lutein, lycopene or their esters, and mixtures thereof.

The invention also provides a method of use of the homogeneous, granular, solid matrix composition defined above wherein said solid matrix is in the shape of granules that are filled into capsules; pressed in tablets; are dispensed in sachets; and admixtured with semi-solid food, solid foods, premixed, or mixed in-situ, in order to form compositions for the administration thereof.

In another aspect of the present invention, there is now provided a process of preparing a homogeneous, granular, solid matrix composition that is substantially insoluble in aqueous medium, and substantially insoluble for at least two hours in gastric juices, and which solid matrix completely disintegrates in the presence of digestive proteolytic enzymes or intestinal juices, said composition comprising at least one bioactive ingestible which is at least partially insoluble in an aqueous medium, wherein said at least one bioactive ingestible is embedded in a substantially molecular or uniform non-crystalline dispersion by the aid of lecithin in a matrix made of at least 10% vegetable proteins which are denatured in said granules, said process comprising the steps of:

a. dispersing or solubilizing said at least one bioactive ingestible in a lecithin-water mixture to form a dispersion, wherein said at least one bioactive ingestible is at least partially water insoluble in an aqueous medium;

b. mixing non-denatured vegetable proteins with the dispersion of step (a) to obtain a wet mass;

c. granulating said wet mass; and d. heat treating the wet granules to above at least 70° C. to denature said non-denatured vegetable protein and to obtain solid dry granules with said at least one bioactive ingestible incorporated therein.

Preferably, in said process the denaturing heat is applied for less then 10 minutes and most preferable for less then 5 minutes.

In a most preferred embodiment of the present invention, the denaturing heat is applied for less then 2 minutes and most preferable for less then 1 minute.

Preferably the ratio of vegetable protein to the combined amounts of lecithin and ingestible bioactive compound is between about 40:1 and 1:4

In especially preferred embodiments of the present the ratio of vegetable protein to the combined amounts of lecithin and ingestible bioactive compound is between about 10:1 and 1:1.

Preferably said ingestible bioactive compound has a water solubility of less than 10 mg/ml at 25° C.

In preferred embodiments of said process, said vegetable proteins are concentrated and isolated proteins selected from the group consisting of: corn, potatoes, wheat, peanuts, beans, rice, sesame, barley, sunflower, canola and rapeseed.

Preferably, said ingestible bioactive compound is selected from the group consisting of a drug, a nutrient, a vitamin, a food supplement, an enzyme, a coenzyme, an oil, omega 3, omega 6, lutein, lycopene or their esters and mixtures thereof.

In preferred embodiments of said process the granules are free flowing and filled into capsules or pressed in tablets.

The invention also provides a composition for releasing bioactive ingestibles, locally in the intestine, whenever prepared according to the above defined process, said composition comprising bioactive ingestibles that are at least partially insoluble in an aqueous medium, wherein said composition is made of a homogeneous dispersion of said bioactive ingestibles in a homogeneous solid matrix comprising lecithin and vegetable proteins, wherein said vegetable proteins are isolated and concentrated vegetable proteins containing at least 40% w/w proteins and said proteins are denatured in said homogeneous solid matrix, and wherein said proteins are at least partially non-denatured before the drying process and are thereafter denatured in said homogeneous solid matrix.

In another aspect of the present invention, there is now provided a method of use of the granules produced according to the above defined process, wherein the granules are filled into capsules, pressed in tablets, are dispensed in sachets, admixtured with semi-solid food, solid foods, premixed, or mixed in-situ in order to form compositions for the administration thereof.

DETAILED DESCRIPTION OF THE INVENTION

Introduction

Figure 1:
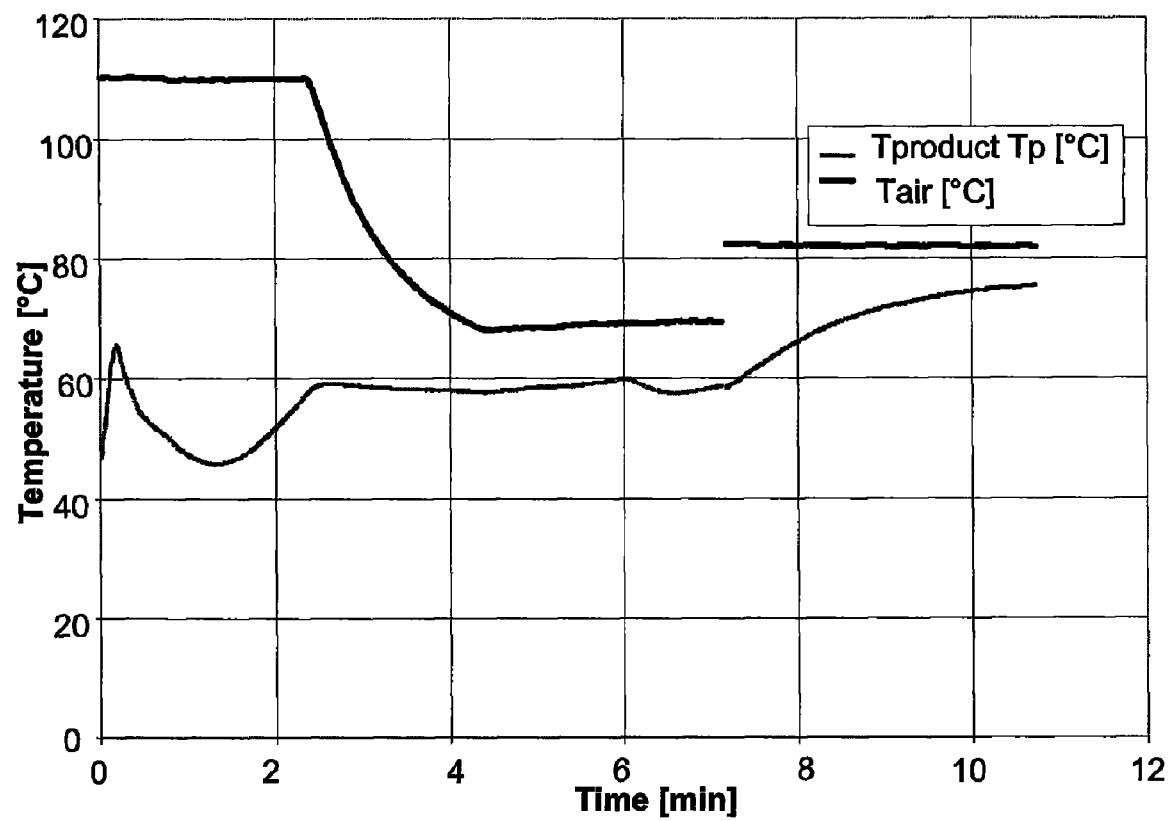
FIG. 1 is a graphical representation of a temperature profile of air and product during lab-scale fluidized bed denaturing and drying performed according to example 26.
Figure 2:
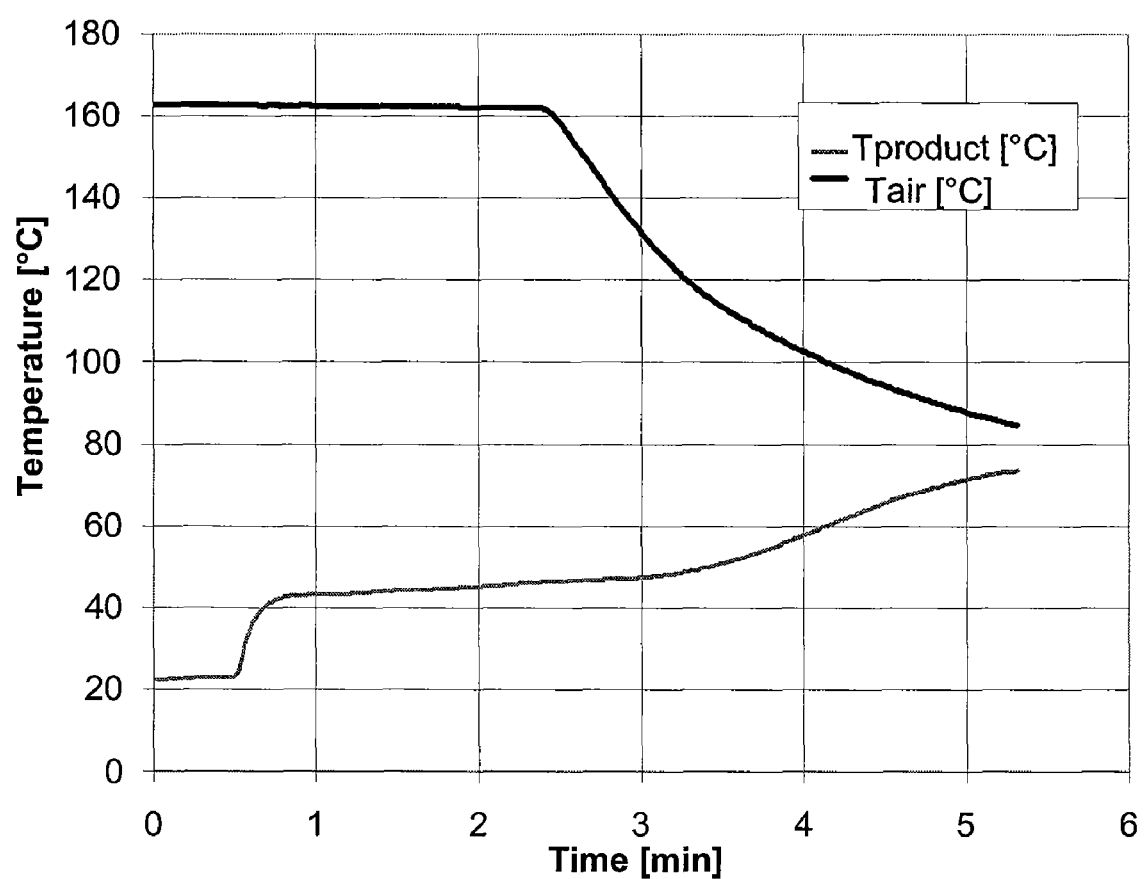
FIG. 2 is a graphical representation of a temperature profile of air and product during lab-scale fluidized bed denaturing and drying performed according to example 23.

A variety of solid matrix compositions and production techniques have been used for years by the pharmaceutical and food industry in order to:
a) convert oily liquids to free-flowing powder,
b) improve the dissolution rates and bioavailability of drugs or nutrients, specifically those that are insoluble or have a low solubility,
c) protect the compounds from decomposition, and
d) mask unfavorable odor or taste.

Such methods and matrices include particular solids in the form of: microcapsules, microspheres, granules, pellets, nano-particles, etc.

Microparticles are spherical polymeric particles ranging in size from greater than one micron, to up to 2000 microns. Microparticles include microcapsules in which the biological agent is uniformly confined within a cavity, and microspheres in which the agent is dispersed throughout the microparticle. The agent may be dispersed in the microparticle matrix as discrete crystals or in an amorphous homogeneous form. Many processes can be used for the preparation of microparticles including solvent evaporation, organic phase separation, interfacial polymerization, emulsion polymerization, and spray drying.

Numerous polymers have been used as matrices for microparticles including polysaccharides, polyesters, and nonbiodegradable synthetic polymers. Polyesters, especially, poly (D,L-lactide-co-glycolide) are desirable for microencapsulation of peptides because aside from being biodegradable or bioerodible, they are also readily available, easily processed and non-toxic.

Matrices and microparticles are also prepared from biocompatible materials such as starch, cross linked starch, starch derivatives and modified starches including: amylodextrin, gelatin, albumin, collagen, dextrin and dextrin derivatives, polyvinyl alcohol, polylactide-co-glycolide, hyaluronic acid and derivatives thereof, such as benzyl and ethyl esters; gellan gum and derivatives, cellulosic polymers, specifically lower alkyl ethers of cellulose in addition to protein polymers such as albumin, sephadex, or DEAE-sephadex.

Other known materials used in manufacturing microparticles include alginates, xanthan gum, and gellan gum. All three substances are effective as enteric coatings. Alginates are known to produce uniform films and are applied in industries as diverse as paper coatings, textile printing, and foods. The alginate film is particularly effective as an enteric coating because it normally is applied as the soluble sodium form, which then is converted to the insoluble alginic acid form by gastric fluids. Improvements have been made by combining sodium alginate with sodium calcium alginate in tablets containing high drug loading.

U.S. Pat. No. 5,972,387 discloses a "modified vegetable protein" to produce microspheres for oral delivery of pharmaceutical agents. The "vegetable protein" is modified with benzene sulfonyl chloride and benzoyl chloride. The present invention makes it possible to produce homogeneous granular solid matrix compositions with non-modified vegetable proteins.

U.S. Pat. Nos. 5,558,880 and 5,684,093 "relate to methods for preparing products by removal of a solid frozen solvent from a frozen matrix mixture". A fast dissolving porous solid matrix is formed, containing small amounts of gelatin, pectin and/or soy fiber protein which act as anti cracking agents and anti meltback agents.

U.S. Pat. No. 5,725,899 "relates to a novel composition of lipoprotein material having emulsification and gel-forming properties and more particularly to such a composition prepared from edible soy flour". This patent discloses the use of a defatted oil-seed protein material, in contrast to the present invention which makes use of concentrated or isolated vegetable proteins. This patent also aims to produce emulsifying and gelling agents and not a solid lipid matrix.

Synthetic proteins are used for microencapsulation. For example, U.S. Pat. No. 5,840,340 uses small proteins, 25 to 2400 daltons or 2 to 20 amino acids, to form "protenoid carriers" with solubility within selected pH ranges, for oral delivery of pharmaceutical agents. U.S. Pat. No. 5,904,936 applies synthetic polyamino acids of specific type in the range of 4,000 Daltons. The present invention utilizes all natural, non-synthetic, vegetable proteins of 25,000 daltons and higher.

Co-precipitation is a common method for obtaining homogeneous, non-crystalline dispersions of an agent in a specific matter. Preparing such solid particles including microparticles, microspheres, microcapsules, nanoparticles, pellets or granules, and the incorporation of ingestible bioactive compounds, involves the use of synthetic polymers and organic solvents. For example, U.S. Pat. No. 6,004,973 uses organic solvent, ethanol/acetone, to produce nanoparticles made of synthetic polymers containing Rafamycin in a non-crystalline amorphous dispersion. U.S. Pat. No. 5,776,495 utilizes a range of organic solvents, such as methylene chloride, alkanols, chlorinated and oxygenated solvents, in order to produce solid co-precipitates. U.S. Pat. No. 5,491,154 employs acetone to co-precipitate dihydropyridines with PVP. U.S. Pat. No. 4,880,623 uses acetone; methylene chloride to co-precipitate Nifedipine with polyethylene glygol and hydroxypropylmethylcellulose; methylcellulose; hydroxypropylcellulose; carboxyvinyl polymers; and xanthan gum. U.S. Pat. No. 4,758,427 teaches solid molecular dispersion of 2-aryl-pyrazolo quinolines with PVP, co-precipitated by the use of methanol. U.S. Pat. No. 4,610,875 makes enhanced dissolution of dipyridamole in amorphous form in PVP, using organic solvents and an agent inhibiting the formation of crystals. The present invention does not make use of organic solvents or synthetic polymers, although it does enable co-precipitation of ingestible bioactive compounds in a homogeneous granular solid matrix made of vegetable ingredients that is substantially insoluble in aqueous medium and substantially insoluble for at least two hours in gastric juices, which solid matrix completely disintegrates in the presence of digestive proteolytic enzymes or intestinal juices.

U.S. Pat. No. 4,404,228 relates to a lipid and protein containing material in particulate form. Such materials are widely used in human and animal foodstuff industries, including calf milk substitutes and coffee whiteners.

Bitter tasting agents are generally administered orally in gelatin capsules or coated tablets, however, other methods for taste-masking of bitter compounds are available, including mixing the substance with taste modifying agents, granulating or microencapsulation. U.S. Pat. No. 5,904,937 discloses use of microcrystaline cellulose for wet granulation of bitter drugs. U.S. Pat. No. 5,728,403 discloses coating technology for taste-masking orally administered bitter drugs. U.S. Pat. No. 5,382,535 discloses "chewable drug-delivery compositions" for oral delivery of unpalatable drugs. The drug is intimately dispersed or dissolved in a pharmaceutically acceptable lipid that is solid at room temperature. U.S. Pat. No. 5,785,984 discloses a "protein-lipid complex which modifies the taste of a food, pharmaceutical or cosmetic". The "protein-lipid complex" agent, interacts with the taste buds to block out and reduce the sensation of bitterness. This patent also teaches the use of organic solvents for incorporating hydrophobic ingestibles. This patent does not teach the use of a homogeneous granular solid matrix made of vegetable ingredients that is substantially insoluble in aqueous medium and substantially insoluble for at least two hours in gastric juices, which solid matrix completely disintegrates in the presence of digestive proteolytic enzymes or intestinal juices, in which ingestible bioactive compounds are embedded in a non-crystalline amorphous manner.

U.S. Pat. No. 5,972,373 discloses compositions for taste-masking and bioavailability with synthetic stomach soluble polymers and a monoglyceride in a beta-crystal form. The disclosed polymers are: polyvinylacetal diethylaminoacetate, aminoalkylmethacrylate copolymer E or a mixture thereof.

U.S. Pat. No. 5,785,984 (Kurihara et al) discloses an emulsion and emulsification process whereas the proteins must be soluble in order to form a complex with the lipids "The emulsification step for preparing the protein-lipid complex according to the present invention can be conducted by the method which comprises premixing a protein with a lipid and dispersing and emulsifying the obtained mixture in a predetermined amount of water, the method which comprises preparing a homogeneous aqueous solution of a protein and dispersing and emulsifying a lipid in the solution or other methods. Any of these methods may be employed. In the dispersion and emulsification, a homogenizer or an emulsifier, an ultrasonic apparatus and the like can be used.

With respect to the emulsifying condition of the emulsion composition, oil-in-water type (O/W type), water-in-oil type (W/O type), multiphase emulsion types such as oil-in-water-in-oil type (O/W/O type), and so forth may be cited. The emulsifying condition is not particularly limited in practice. It is preferable that the particle size of the dispersed phase of the emulsion composition be 0.1 to 100 .m□.m, particularly preferably 0.5 to 10 .mμ.m."

In contradistinction, according to the present invention, there is no emulsification step, the phospholipids are not first mixed with active ingredient, and the proteins are not allowed to emulsify or be dispersed in water.

Moreover, U.S. Pat. No. 5,785,984 (Kurihara et al) indicates that it is important to avoid an excess of heat. As stated therein, "Although the temperature at which the blending of a protein with a lipid or the dispersion of a protein and a lipid in water is conducted is not limited, the employment of high temperature causes the degradation of the lipid or the like and the generation of a bad smell in some cases. Accordingly, it is preferable that the temperature be 60.° C. or below to prevent such adverse effects. The method of the dehydration is not particularly limited, and known methods can be employed. Examples of the method of the dehydration include means such as vacuum drying, spray drying and freeze drying. It is desirable in the present invention to employ a method which permits rapid dehydration without causing the degradation of the lipid and protein and the contamination with microorganisms."

In contradistinction the present invention is based on utilizing excessive heat, i.e., a temperature of at least above 70° C., and is based on a process which in effect destroys the proteins and causes a change in their physical properties so that they become denatured. The present invention is directed to a homogeneous granular solid matrix made of vegetable ingredients that is substantially insoluble in aqueous medium and substantially insoluble for at least two hours in gastric juices, which solid matrix completely disintegrates in the presence of digestive proteolytic enzymes or intestinal juices, and thus which is only disintegrated by the natural mechanism of enzymatic degradation in a mammal's digestive system, particularly by the proteolytic enzymes of the small intestine.

JP 5320057 describes a composition for treating constipation, comprising a mixture of chondroitin salts and lecithin and protein. The composition is not intended for delivering drugs and is not intended for withstanding gastric degradation and site specific intestinal drug release by the mechanism of enzyme digestion. JP 5320057 does not disclose a method of denaturing proteins and obtaining granules that show a specific method of disintegration.

U.S. Pat. No. 3,303,182 describes a method of producing fully soluble denatured proteins. In contradistinction, the present invention is directed to a composition which is at least partially insoluble in aqueous medium and does produce colloidal systems in water, and to a process for the preparation thereof. The granules of the current invention do not dissolve or disintegrate in water.

U.S. Pat. No. 3,914,443 describes meat-like foodstuffs made of denatured proteins. U.S. Pat. No. 3,914,443 uses denatured soy proteins in combination with gelatin, as starting material and is aimed at producing soft fiber meat-like food stuffs, which are as soft and chewable as meat, whereas the product of the current invention is a solid material which does not swell or soften in the mouth and is obtained by the processing of non-denatured vegetable proteins under specific process conditions and which material disintegrates only in the presence of proteolytic intestinal enzymes.

DE 4342124 describes a tablet that may comprise proteins, apparently as a binder or tablet filler. In said publication there is no teaching of a protein denaturing state nor is there a teaching of a disintegration process or mechanism of solid particle disintegration controlled by enzymes or proteolytic enzymes. Said publication also does not teach or suggest a process of using non-denatured proteins which are denatured in order to obtained desired solid particles which are disintegrated only in the presence of proteolytic enzymes. DE 4342124 does not discuss the homogeneous dispersion of bioactive agents of low solubility in the tablet matrix.

None of the above patents, i.e.: JP 5320057, U.S. Pat. No. 3,303,182, U.S. Pat. No. 3,914,443 and DE 4342124, teach a homogeneous dispersion of bioactive agents which are at least partially insoluble in aqueous medium in a process involving solubilizing the bioactive agent in concentrated lecithin hydrated in water.

Furthermore, none of said references teach or suggest a heat treatment of wet granules at a temperature above at least 70° C. to denature non-denatured vegetable protein and to obtain a dry homogeneous granular solid matrix made of vegetable ingredients that is substantially insoluble in aqueous medium and substantially insoluble for at least two hours in gastric juices, which solid matrix completely disintegrates in the presence of digestive proteolytic enzymes or intestinal juices.

Detailed Embodiments

Thus according to the present invention there is provided a novel composition of a homogeneous granular solid matrix made of vegetable ingredients that is substantially insoluble in aqueous medium and substantially insoluble for at least two hours in gastric juices, which solid matrix completely disintegrates in the presence of digestive proteolytic enzymes or intestinal juices, for administration of ingestible, bioactive compounds which are at least partially insoluble in aqueous medium, and which composition improves gastro-intestinal dissolution and consequent oral availability or bio-compatibility, in addition to taste-masking of bitter drugs, nutrients, food additives, vitamins, minerals or phytomedicines.

According to a preferred embodiment of the present invention, the hydrophobic bioactive and ingestible ingredients are solubilized and/or co-melted with required amounts of a lecithin-water mixture, until homogeneity is achieved. Homogeneity is defined as the absence of a crystalline form of the ingestible bioactive compound. The homogeneous wet mixture is further mixed with vegetable proteins until homogeneity is achieved, and sufficient water is then added to produce a desired consistency appropriate for screen granulation, sieving and shaping. Said mixture is finally molded, the proteins are denatured by heat, and the granules are further dried to obtain the desired shape. The final steps of mixing with vegetable proteins, denaturing the proteins, and the drying step, may also be accomplished simultaneously, by utilizing different procedures, e.g., spray drying.

According to a preferred embodiment of the present invention, the solubilization is a solvent-free process whereby the hydrophobic, low or poor water soluble compounds, are substantially solubilized within the hydrated lecithin aggregate's hydrophobic and amphiphilic micro-environments.

Various vegetable proteins possess a diversity of functionality levels, which directly influence the matrix formation, its density and the required amount of protein needed to obtain the matrix. More functional vegetable proteins form a denser, three dimensional network, enabling the formation of the matrix at a lower protein concentration or form a much tighter condensed matrix.

The active compounds are released from the homogeneous solid matrix in a non-immediate manner. By selecting proteins with different functionality levels and at different concentrations, the extent of delaying the release is controlled. For purposes of masking bitter taste, there is a need for a short delay of release, while the granules are passing through the oral cavity. A hydrophobic compound will be released from a very tight matrix in a slow release manner. The current invention enables control and design of the release pattern from a very short release delay for the purpose of taste masking, to a prolonged delay of as long as a couple of hours for effective absorption and for the lowering of the number of daily administrations.

The granules show minimal swell in water, do not disintegrate in a simple aqueous medium, or at different pH conditions. The granules disintegrate by a digestive process activated by intestinal proteolytic enzymes. The granules release less then 20% of the bioactive ingestible in the stomach and the majority of the bioactive nutrient or drug is released in the small intestines by a process of matrix erosion, which depends on local duodenal and small intestinal proteolytic enzymes.

Water soluble, hydrophylic compounds will be very quickly released from the matrix, whereas hydrophobic compounds will mostly be released in the small intestine as the proteins are digested and the matrix decomposes.

Thus, in preferred embodiments of the present invention, said matrix provides for the release of said ingestible bioactive compound over a period of one to three hours in the gastro-intestinal tract.

In especially preferred embodiments of the present invention the limiting step for the ingestible bioactive compound release is the gastro-intestinal digestion of said proteins and decomposition of the matrix.

The release rate is also influenced by the amount of lecithin in the matrix. A high lecithin concentration enhances the release profile due to better hydration, swelling and decomposing of the matrix.

As defined hereinbefore, the compounds of the present invention are at least partially insoluble in an aqueous medium and especially preferred are ingestible bioactive compounds having a water solubility of less then 1.0 mg/ml at 25° C.

As stated, in the process of the present invention, the denaturing process is performed by heating the wet granules to above 70° C., preferably followed by drying, wherein both processes are performed by heating, by circulating hot air, by microwaving, by a combination of heat and vacuum, by lyophilization or by spray drying.

According to a further preferred embodiment of the present invention, the ingestible bioactive compound or mixture is homogeneously embedded in the final matrix in a manner by which the original crystals or powder or amorphous solid are solubilized, and the dispersability in the matrix is uniform, so that the matrix is a monolithic entity, made up of an even homogeneous distribution of the various ingredients; including the active agents and excipients.

According to a preferred embodiment of the present invention, additives, such as fumed silica, may be added before or after drying, in order to enhance the flow properties of the resulting powder.

Furthermore, according to a preferred embodiment of the present invention, additives such as pharmaceutical or food grade emulsifiers, or gliding agents, may be added before or after drying, in order to enhance the free flowing properties of resulting powder.

According to a preferred embodiment of the present invention, the composition may include additives such as colorants, anti-oxidants, preservatives, etc. known in the art for nutraceuticals, food or medicines.

According to a preferred embodiment of the present invention, the composition may include within the primary composition or added to the post drying product, taste and flavoring agents known in the art for nutraceuticals, food or medicines, such as fruit flavors or instant fruit powders for reconstitution as a beverage.

According to a preferred embodiment of the present invention, the resulting dry solid matrix may be shaped as granules, pellets, microspheres, or nanoparticles, in addition to irregular shapes of various sizes and quantities.

The ratio of the amount of hydrophobic bioactive mixture or bitter compound, and the lecithin and vegetable proteins, is adjustable according to the nature of the bioactive compound, and is adequately designed by those skilled in the art.

The compositions are well suited for pharmaceutical use, complementary medicine, nutraceutical and veterinary use, as well as for oral consumption of products in the shape of bars, nuggets, tablets, capsules, coated tablets or capsules, dissolve-in-the-mouth tablets, effervescent tablets or powder, concentrated powders, as well as for incorporation in juice or beverage preparations and confectionery products, etc.

According to another embodiment of the present invention, there is provided a method of releasing the ingestible bioactive agent from the homogeneous solid matrix.

Hereinafter, the term "subject" is the human or mammal to which the homogeneous matrix of the present invention is administered.

In another aspect of the present invention, there is provided a method for preparing the above described composition, wherein lecithin is swollen in water in a ratio of between about 1:3 to 1:10, more preferable 1:5 to 1:8, and said ingestible bioactive compound is added until complete solubilization, functional vegetable proteins are then added with additional water, if necessary, and in quantities sufficient, to produce granulation dough, whereafter the wet mass is granulated and the protein is denatured at a temperature above 70° C. and preferably above 90° C. and solid matrix is dried to less than 10 percent water content, preferably less then 7.5 percent water content, and more preferably to less then 5 percent water content.

In another embodiment, the resulting granules are spread evenly on large pieces of paper in shallow trays and dried in a dedicated regulated heat oven, hot circulating oven, microwave oven, under reduced pressure and temperature, or a fluid bed drier.

In preferred embodiments of this method said wet mass is further diluted with water and spray dried.

In further preferred embodiments of said method, the wet granulation is extruded through a screen having openings of 0.5 mm to 2.5 mm and spheronized in a spheronizer.

In yet further preferred embodiments of said method the wet granulation is prepared and formed into spheres, utilizing a high shear granulator to form taste-masked spheres.

Preferably, said method is applied to an ingestible bioactive compound, which is a bitter tasting compound, wherein homogeneous particles and taste masking properties are obtained.

Functional vegetable proteins that are suitable for solid matrix forming have the following physico-chemical characteristics:
A) high molecular weight of 50,000 Daltons and higher;
B) NSI (nitrogen solubility index) of at least 10% and preferably higher then 20%; and
C) non-denaturated or only partially denaturated proteins.

Therefore, said vegetable proteins are non- or minimally denatured, having at least 10% NSI with a preferred NSI of 20%, and an even more preferred higher NSI, and a MW of not less then 50 kD with a range of 100,000 to 300,000 MW, non- or minimally hydrolyzed.

Vegetable proteins may be protein concentrates or protein isolates selected from the group consisting of: soy (soybeans), wheat and wheat germ, barley, sesame, pea, rice, beans, peanuts, potatoes, legume, corn, sunflower, canola or rapeseed.

Said functional vegetable protein isolates or concentrates contain at least 65% proteins and at least 5 NSI (Nitrogen Solubility Index) and with water absorption values of at least 100% and MW>25 kD.

The soybean, Glycine max, is a leguminous crop grown in many parts of the world. Soybeans are of great economic importance as a source of edible oil, high-protein foods, food ingredients, and stockfeed, as well as being a source of many industrial products. Native to Eastern Asia, the soybean has been used as the chief source of protein for millions of people in the Orient, for centuries. It was not until the late 19th century, however, that soybeans began to attract serious attention from Western scientists.

The term "soy proteins" typically refers to processed, edible dry soybean products, other than soybean meals for animals.

Soy protein products, for human consumption, fall into three major groups:
(a) soy flours and grits having 52 to 54% protein (N.times.6.25) on a moisture-free basis (mfb),
(b) soy protein concentrates containing at least 65% protein (N.times.6.25) mfb, and
(c) soy protein isolates (or soy proteinates) having a minimum of 90% protein (N.times.6.25) mfb.

The term "% Protein (N.times.6.25)" is often used to express the percentage of protein in soy protein products in order to reflect that only part of the nitrogen in soy proteins is of protein origin. The American Oil Chemists' Society (AOCS) conversion factor for soybean protein is N.times.5.71; however, industry practice is to label protein in soybeans as "Protein (N.times.6.25)."

Soy flours and grits are the least refined forms of soy protein products used for human consumption and may vary in fat content, particle size, and degree of heat treatment. These products also still contain about five (5) to six (6) percent of the oligosaccharides and most of the original lipoxygenase, as well as about 4.3% fiber. As a result, they can only be used in small amounts in various products; otherwise intestinal discomfort and poor flavor become the overriding consideration. Soy flours and grits are considered to be "poorly" functional and typically have an NSI less than about 60%.

Soy protein concentrates have much of the indigestible oligosaccharides removed and therefore the raffinose content is less than about 0.5% and the stachyose content is less than about three (3)%. However, depending on the process used, soy protein concentrates have only poor to adequate flavor, and low to adequate functionality, having NSI's in the range of 15-70%. Additionally, the various processes for producing soy protein concentrates, result in a recovery of only about 50% to 95% of the protein. In every instance, the high cost of such processes limit the use of these products in many areas, such as aquacultural diets, poultry diets, and so forth. Furthermore, the presence of approximately four (4)% fiber in soy protein concentrates makes them unsuitable for use in certain products such as beverages, milk and infant formulas. The current processes also remove important vitamins, minerals, isoflavones and phytoestrogens along with the low molecular-weight sugars, ash, and minor components.

Soy protein isolates are the most highly refined soy protein products commercially available, as well as the most expensive. As with the soy protein concentrates, soy protein isolates are also low in oligosaccharides, having negligible amounts of raffinose and less than two 2(%) stachyose in the final product. Additionally, the isolates have a satisfactory flavor and are highly functional, having a NSI in the range greater than about 85%. Isolates also improve dispersibility and reduce dusting. Both gelling and non-gelling varieties are available in addition to various viscosity grades. They possess a low fiber content of less than about 0.3%. As discussed above, it is desirable to remove the fiber in certain products because fiber is non-functional and dilutes protein content.

Soy Protein Concentrates: Concentrates produced by the aqueous alcohol and heat treatment/water extraction processes have low nitrogen solubility because of protein denaturating. In contrast, the products made by aqueous acid leaching or by steam injection/jet cooking, and subsequent high shear treatment, have higher solubility if neutralized prior to drying. These concentrates vary in particle size, water and fat absorption properties and flavor. They all have improved flavor characteristics compared to commercially available soy flours. They provide several functional characteristics in forming fat emulsions in food systems such as fat-micelle stabilization, water and fat absorption, viscosity control and textural control. Many of these characteristics are inter-related in a stable food system. Both pH and temperature affect the emulsifying properties of soy concentrates.

Soy concentrates contain polysaccharides, which absorb a significant amount of water. Processing conditions can vary the amount of water that can be absorbed. In fact, these conditions can be varied to influence how tightly the water is bound by the protein in the finished food product.

Since the acid leach and steam injection/jet cooking processes can result in a product with higher dispersibility, these concentrates are more desirable for functional properties in emulsion-type applications. Nevertheless, all soy protein concentrates, regardless of the process used, do have certain fat and water-retaining characteristics.

Soy Protein Isolates: Isolates have specific functional properties that enable them to modify the physical properties of food products. Soy isolates are characterized by certain functional properties i.e., solubility, gelation, emulsification, dispersibility, viscosity and retort stability.

Solubility ranges from 5 NSI (Nitrogen Solubility Index) to 95 NSI. The emulsion capacity of soy protein isolates can vary from 10 to about 35 milliliters of oil per 100 milligrams of protein. Isolates have water absorption values of up to 400%.

Neutralized isolates are usually highly soluble; certain types will gel under appropriate aqueous conditions. They possess both emulsifying and emulsion-stabilizing properties, are excellent binders of fat and water, and are good adhesive agents. They vary mainly in their dispersibility, gelling and viscosity characteristics.

Soy protein isolate aids in forming a gel which acts as a matrix for holding moisture, fat and solids. This results in textural properties resembling those of meat proteins, which is especially important for use in comminuted meats and non-meat items such as tofu. Its ability to form a gel (from fragile to firm) depends on concentration, functionality and the presence or absence of salt. Some isolates are designed not to form a gel even at a 14% solids content.

Gelation is the formation of three dimensional, intermolecular networks through hydrogen, hydrophobic, and disulfide bonds that entrap water solvent and other ingredients. This is another aspect of hydration and of textural and rheological properties of protein; further defined as the formation of three dimensional intermolecular networks through hydrogen, hydrophobic, and disulfide bonds that entrap water and other ingredients. This entrapment contributes to the texture and chewiness of the food products. The important initial step in heat-induced gelation of globular proteins, is the heating of the protein solution above the denaturating temperature to expose the functional groups, so that the intermolecular network can be produced. Additionally, high numbers of intermolecular disulfide bonds increase water holding capacity, and, as a result, increases gel hardness.

Wang and Damodaran (1990) studied the thermal gelation of globular protein of bovine serum albumin (BSA), soy isolate, 7S, 11 S, and phaseolin. They reported that gel hardness or strength of globular protein gels is fundamentally related to the size and shape of the polypeptide in the gel network, rather than to their chemical nature, such as amino acid composition and distribution. Globular protein with MW<23 kD cannot form a self-supporting gel network in any reasonable concentration.

The homogeneous solid matrix is formed during the drying process, whereby the vegetable proteins form the solid matrix by constituting molecular connections between the proteins in a similar or equal process to denaturating.

Examples of commercially available isolated soy proteins are the Supro™ types 810, 760 and EX 34K and others from Protein Technologies International, St Louis, Mo., USA and Soyarich™ from Central Soy Protein, USA. Examples of concentrated soy proteins are Solcon™ HV, and other brands from ADM and Cargill both of USA.

Vegetable proteins are selected from any vegetable, such as soy proteins or wheat proteins, whereas wheat proteins may be gluten or gluten free. An example of isolated soy protein is Supro™ of various types and examples of isolated wheat protein is Gemtech™ of various types and Prolite™ from ADM.

Lecithin is a mixture of phospholipids from vegetable or animal origin; e.g. these may be obtained from soybean, wheat, corn or eggs. More preferably, the lecithin concentration is equal to the amount of the bioactive compound and is present in an amount of not less then 1 percent and up to 50 percent.

Phospholipids are the main building blocks of all cell membranes—in human beings, animals, plants and micro-organisms. As such they have two important physical and chemical properties which are being put to increasing use in pharmaceutical technology, i.e., they are:

1) amphiphilic molecules which contain excellent emulsifying properties; and
2) (under certain conditions, especially with respect to concentration and temperature) phospholipids which spontaneously form membrane structures (lamella, liposomal, micellar).

Products having such properties include vegetable (mainly soybean) and animal phospholipid mixtures (egg) with greatly differing compositions and properties, and also hydrogenated products that are especially useful for their resistance to oxidation. Lecithin may also be obtained from various vegetable origins, for example from oatmeal, wheat germ or peanuts.

Historically, the term lecithin originated from the Greek word 'lekithos', which was used for the phosphorus containing lipids from egg yolk. Later, this term was only used for one defined phospholipid, phosphatidylcholine. This is still the common usage in scientific literature, where lecithin stands for 1,2-diacyl-glycero-3-phosphatidylcholine. In contradistinction, the term lecithin is used in industry and commerce to refer to a complex mixture of neutral lipids (predominantly triglycerides, a small amount of free fatty acids and sterols), polar lipids (phospho- and glycolipids) and carbohydrates.

The technological and physiological properties of lecithins are primarily determined by the kind and portion of the various polar lipids, especially the phospholipids. It is evident that these compositions may vary considerably, depending on the origin of the soybeans. Climate, soil conditions, harvest time and, last but not least, processing conditions, also greatly influence the composition and properties of lecithin.

The molecular structure of phospholipids is derived from the structure of triglycerides by replacement of one fatty acid by a phosphoric acid ester. Depending upon the molecule (predominantly an aminoalcohol) linked to the phosphate group, the various phospholipids are referred to as follows:
Choline=Phosphatidylcholine (PC)
Ethanolamine=Phosphatdylethanolamine (PE)
Inositol=Phosphatdylinositol (PI)
Hydrogen=Phosphatidic acid (PA)

By virtue of their amphiphilic molecular structure with the hydrophilic phosphoric acid ester and the lipophilic fatty acids, phospholipids in oil and water systems always concentrate at the interphase. This typical emulsifying property is the reason for their successful use in a variety of foodstuffs, dietetic, cosmetic and pharmaceutical preparations.

Lecithin is described as a generally permitted food additive in Europe under E 322 and in the US in the Code of Federal Regulations (GRAS status) referring to the Food Chemical Codex. These descriptions differ from each other to a minor degree in their specification details, but not in principle.

Examples of commercially available lecithins are, Phospholipons from Natterman™, Epikuron™ from Lucas Meyer, pure lecithin powder de-oiled from Stern™, all from Germany, and others.

Insoluble or low water soluble ingestible bioactive compounds may be any chemical, drug, molecule, substance, extract, herbal, vitamin, synthetic or semisynthetic or biotechnology product, hormone, peptide, protein, or mixture comprising such ingredient, that has a desired and/or required bio-activity, and its biological activity is reduced, limited or is practically erratic, due to low or poor water solubility and low dissolution or wetting and insufficient concentration at the absorption or administration or biological target site. Most preferably, the bioactive compound is present in an amount of from about 0.1 percent to 50 percent weight of the final product, more preferably in the range of 1.0 to 30%, and is practically dictated by its bio-active dose relevant for the specific use, purpose, expected results and physico-chemical formulation properties.

Hydrophobic, water insoluble or lipophilic agents and low or poor water solubility compounds, as used herein, refer to ingestible agents, having a water solubility of <10 mg/ml and more preferably <1 mg/ml and, even more preferably, <0.5 mg/ml in water, at room temperature (25.degree. C.).

Most phytomedicinal extracts are mixtures or assemblies of many types of molecules, usually comprising a fraction that is water insoluble or has low water solubility. With regard to proper and effective herbal extracts, solvents such as alcohol or propylene glycols or glycerin, and hexane or cyclohexane, are frequently and abundantly employed in phytomedicinal extract production. Another method for herbal extraction of water insoluble precious bioactive compound, is lipid extraction, hot or cold compression and super fluid extraction. All these methods are employed in order to obtain herbal fraction with poor water solubility. The non-aqueous extracts are important constituents of the majority of herbal bioactive products. Apart from a few exceptions, most top marketed herbal extracts contain some hydrophobic active molecules of poor water solubility. Many of the herbal extracts, especially those extracted from lower underground root parts of the herbs, are also typically bitter.

Examples of herbal, poorly water-soluble, or mixtures comprising hydrophobic phytomedicines are: *Gingko biloba, Hypericum perforatum, Echinacea purpurea* or *angustifolia*, Ginseng, *Piper methisticum* (Kava), *Tanacetum parthenium*, and *Allium sativum* (Garlic).

Examples of lipophilic vitamins include: Carotenoids and lycopene, Lutein or Lutein esters, Tocopherols (Vit E) or esters thereof, Riboflavin (Vit B2), Retinol (Vit A), Calciferol (Vit D2), Cholecalciferol (Vit D3), Menadion (Vit K), Folic acid and ubiquinones.

Oily substances, include fish oil, omega 3 oils, omega 6 oils, fish oil concentrates, docahexanoic and eicosapentaenoic acid or esters and mixtures thereof, alpha linolenic acid, gama linolenic acid, arachidonic acid, evening primrose oil, flaxseed oil, black currant oil, borage oil and mixtures thereof.

Absorption of lipophilic vitamins is much more limited in comparison to water-soluble vitamins. Fortunately, only very minute quantities of vitamins are required for normal living, however, elderly people who need them more, less effectively assimilate vitamins and essential nutrients. Another population in great need of a sufficient supply of vitamins is the cancer chemotherapy and radiation patient population, who suffer from mal-absorption syndrome and would benefit from an improved delivery of vitamins and essential nutrients.

A bitter taste compound is any drug, nutrient, vitamin or food supplement or phytomedicine of herbal origin compound, which exerts a rejecting unpleasant bitter bad taste. Bitter taste is associated to hydrophobic compounds or the like, having hydrophobic moiety. Most bitter compounds are lipophilic (fat loving). Examples of bitter taste forming substances that exhibit unpleasant oral taste are: aloe barbadensis extracts, barbeloins, *Artemisia* species and various absinthes, gingko biloba extracts, gentian, artichoke leaves, centaury, *aloe* species, barberry, dandelion, wormwood or mugwort (or other *Artemesias*) and blessed thistle. Some of the common bitter herbs are dandelion (*Taraxacum officinale*) and chicory (*Cichorium intybus*), whose roots have been used in coffee drinks. Beer is made from bitter hops (*Humulus lupulus*). Other bitters include: alfalfa, endive, arugula, spinach, unripe apples, citrus peel, scallion, rye, turnip, white pepper, and celery. The bitterest herb in the medicinal herb garden is wormwood. Some less bitter common nutrients are: hesperidine, limonene, and anthocyanines derived from fruits or vegetables.

Drugs have bitter taste are for example, NSAIDs, ibuprofen, paracetamol and the like, antibiotics such as Azitromycin, erythromycin and the like, and beta-blockers such as Propranolol, and Quinine, to name but a few.

Denaturing and Disintegration of Granules

In their functional non-denatured state proteins are flexible polymeric material with some three dimension configuration and they are practically soluble in water.

Upon denaturing, however, the protein becomes rigid, has a much reduced degree of conformational freedom, and becomes practically non-soluble in water, thereby allowing for the production of "solid granules".

Once the granules are produced, the primary mechanism for "destroying" the granules is cleavage or digestion of the denatured proteins of the granules matrix. Thus water alone will not be able to solubilize or disintegrate the granules within a reasonable amount of time necessary to enable the oral absorption of the bioactive agent.

Production Process

A) Mix the lecithin in water to hydrate and swell the lecithin;
B) Disperse or solubilize the bioactive components in the lecithin water of step (A) until homogeneity is obtained;
C) Mix the non-denaturated vegetable proteins with the bioactive components in lecithin water of step (B) to obtain a wet mass of desired consistency for granulation, adding as much or as little water as necessary;
D) Granulate the mixture of non-denatured vegetable protein and lecithin and water and bioactive the wet mass of step (C);
E) Denature the proteins by heating the wet granules to a temperature of above 70° C.; and
F) Dry the denaturated granules.

Lecithin is hydrated and swelled in a minimal amount of water (a preferred ratio of lecithin to water is 1:3 to 1:10. The preferred amounts of lecithin, bioactive compounds and hydrophobic ingestibles, are ratios of 2:1 to 1:2 and more favorably, 1:1 on a dry weight basis. The ratio amount of obtained solubilized bioactive compound in lecithin to vegetable protein is 10:1 to 1:20, and more preferably 3:1 to 1:1 on a dry weight basis.

The granules mean size is principally controlled by the granulation process and equipment. Granules size obtained is from 100 microns to 5,000 microns, and preferably from 300 to 1,000 microns. Granules that are below ~500 microns are usually not chewable and are not crunchy alone or while added to foods, while larger size granules may cause crunchiness to foods and are realized to affect food perception in the mouth.

The denaturing is performed by heat or heat shock, by any means of heat transfer, such as by using an oven, hot air, a microwave or hot plate. The denaturating process is performed in a short time to avoid degradation of the bioactive agent. Heat or heat shock denaturating process is performed above 70° C.; preferable at a temperature above 100° C. At above 100° C., the water evaporates quickly and the granules' temperature is kept below 100° C. As the granules' temperature increases, usually above 90° C., the denaturing process is completed and further drying is continued until the water content of the dry granules is less than 10% and preferably less then 7% and more preferably less then 5%. The water content is measured as "loss on dry" by placing a sample of the granules or solid matrix in a weighing oven at 110° C. and calculating the lost weight after one hour.

The denaturing process should be performed in the shortest time possible in order to avoid degradation of the bioactive components. The denaturing process is carried out preferably within about two minutes; however the denaturing process may be as short as 20 seconds, depending on sample size, heat source, heat distribution, instrumentation, and the specific formulation. Denaturing should be shorter then 10 minutes and preferably less then 5 minutes.

After the denaturing is completed, the drying process is performed by one skilled in the art, in a drying oven, a hot plate, a vacuum dryer, a fluidized bed and the like. The drying process is performed at a temperature as low as possible in cases of heat sensitive bioactive components. Applied heat and water evaporation converts the vegetable proteins into a state that favors intermolecular interactions.

The composition may be used for oral delivery, taste masking, further enteric coating or coating or for immediate release into the mouth. It can also be incorporated into bars, nuggets, chocolate, biscuits, bakery products, solid foods and powders for in situ beverage reconstitutions and the like. The composition may be mixed with flavoring agents such as fruit flavors, natural or artificial flavors, to make the product more appealing to the user.

Various delivery systems and dosage forms are possible, including oral capsules, tablets, and sachets containing the granules or dry suspensions for dilution before use. The compositions can also be incorporated in instant beverages, and instant soups and also incorporated into solid bars or nuggets.

It should be noted that the above descriptions are intended only to serve as examples, and that many other embodiments are possible, within the spirit and the scope of the present invention.

Examples of lipophilic substances that exhibit poor oral bioavailability include: lipophilic drugs, vitamins, NSDA steroids, anti-fungal agents, antibacterial agents, antiviral agents, anticancer agents, anti-hypertensive agents, anti-oxidants, anti-depressants and phyto-chemicals combining herbal extracts.

Low, or poor water soluble compounds, include: fatty sterols of saw palmetto, carotenes and lycopenes, Luteins and esters, Omega 3 and Omega 6 oils and their esters, non-aqueous soluble fractions of *echinacea*, ginseng and *gingko biloba*, in addition to many minerals, such as zinc, iron and multivitamins, and coenzymes, such as ubiquinones.

After mixing with body fluids, the homogeneous solid matrix composition absorbs water and swells. Following hydration and swelling, the release of the bioactive ingestible takes place in the small intestines. The unique matrix and its ingredients as well as the homogeneous dispersion of the bioactive ingestible within the matrix, promotes the solubilization, micelization and emulsification of the insoluble bioactive ingestible, thus enhancing dissolution and bio-availability.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

*Aloe Vera* S.D. and Concentrated Soy Proteins

Barbeloin and its derivatives are some of the bitterest extracts. *Aloe Vera* S.D. (frutarom meer) is a very bitter powder—a non-diluted, concentrated extract characterized by a large fraction of many water insoluble ingredients.
- A) One gram of soybean lecithin, (pure lecithin powder, de-oiled, Stern, Hamburg, Germany) was mixed and swelled in 5 ml of water at room temperature.
- B) Half a gram of *Aloe Vera* S.D. dry extract (frutarom meer) was added and well mixed to obtain a homogeneous fluid paste.
- C) Two grams of functional soy proteins concentrate (Solcon™ HV, Solbar, Ashdod, Israel), were added and mixed well with a sufficient amount of water to produce a homogeneous mass in the appropriate consistency for passing through a granulating net.
- D) An obtained wet mass was mesh granulated and dried in oven preheated for 110 degrees Celsius and reduced to 70 degrees Celsius 2 minutes from drying process start or processed two minutes in microwave oven on high energy and continuous drying in vacuum microwave oven or air oven. An obtained wet mass was mesh granulated and dried in an oven preheated to 110° C. and then the temperature was reduced to 70° C. 2 minutes prior to the beginning of the drying process. Alternatively the wet mass was processed for two minutes in a microwave oven on high energy followed by continuous drying in a vacuum microwave oven or air oven.

Three aliquots, equivalent to 10 mg of *Aloe Vera* S.D. powder in 10 ml of water, were prepared and their bitterness evaluated:
1) Non-treated, *Aloe Vera* S.D. powder in water was so bitter that it was almost impossible to keep in the mouth, requiring many mouthwashes afterwards, and still left a long-lasting bitter taste.
2) *Aloe Vera* S.D. in water with added lecithin and Solcon™ HV was equally as bitter.
3) *Aloe Vera* S.D. granules, prepared according to the present example, equivalent to 10 mg *Aloe Vera* S.D. suspended in 10 ml water was devoid of the original bitter unpleasant taste, and contained no after taste at all.

The granules were tested and found to have less then 5 percent bound water as measured as "loss on dry" by placing a sample of the granules or solid matrix in a weighing oven at 110° C. and calculating the lost weight after one hour.

Example 2

*Aloe Vera* S.D. and Isolated Soy Proteins

- A) 0.5 gram of soybean lecithin, (Phospholipon™ 90, Natterman, Germany) was mixed and swelled in 4 ml of water at room temperature.
- B) 0.5 gram of *Aloe Vera* S.D. dry extract (Frutarom Meer) was added and well mixed to obtain a homogeneous fluid paste.
- C) 1.0 gram of functional soy proteins isolate (Supro™ EX34K, Protein Technologies International, USA), and 0.5 gram microcrystaline cellulose (Avicel™ HP101, FMC, USA) were added and mixed well with QS of water to produce a homogeneous mass in the appropriate consistency for passing through a granulating net.
- D) An obtained wet mass was mesh granulated and dried in ovens or microwave ovens as described in example 1.

*Aloe Vera* S.D. soy protein granules, prepared according to the present example, and suspended in water were found to be devoid of the bitter unpleasant original taste and after taste. The granules were tested to have less then 7 percent bound water as measured as "loss on dry" by placing a sample of the granules or solid matrix in a weighing oven at 110° C. and calculating the lost weight after one hour.

Example 3

*Artemisia Abrotantum*

Artemisin and its derivatives are also extremely bitter. *Artemisia abrotantum* (in house hot maceration, commonly called "Shiba") is a very bitter concentrated extract of *Artemisia abrotantum*, characterized by large fraction of many water insoluble ingredients.
- A) One gram of soybean lecithin, de-oiled, and powdered (Epikuron™ 100, Lucas Meyer, Germany) was mixed and swelled in 2 ml of *Artemisia abrotantum* extract.
- B) Two grams of functional soy proteins (Solcon™ HV, Solbar Ashdod, Israel), was added and well mixed with QS of water to produce a homogeneous mass in an appropriate consistency for passing through a granulating net.
- C) Obtained wet mass was granulated and dried in an oven or microwave oven as described in example 1.

Three aliquots equivalent to one ml of *Artemisia abrotantum* extract in 10 ml of water were prepared and their bitterness evaluated:
1) *Artemisia abrotantum* extract in water was so bitter that it was almost impossible to hold in the mouth and required many mouthwashes afterwards and left a long-lasting bitter taste.
2) *Artemisia abrotantum* extract in water with lecithin and Solcon™ HV and slight vortex was equally as bitter.
3) *Artemisia abrotantum* granules, prepared according to the present example, were devoid of the original bitter taste, contained no after taste at all.

The granules were tested to have less then 7 percent bound water as measured as "loss on dry" by placing a sample of the granules or solid matrix in a weighing oven at 110° C. and calculating the lost weight after one hour.

Example 4

*Artemisia Abrotantum*

- A) 1.0 gram of soybean lecithin, de-oiled, and powdered (pure lecithin powder, de-oiled, Stern, Hamburg, Germany) was mixed and swelled in 10 ml of *Artemisia abrotantum* extract.
- B) 2.0 gram of concentrated soy proteins (Solcon™ HV, Solbar Ashdod, Israel), and 0.5 gram of soy proteins isolate (Supro™ EX34K, Protein Technologies International, USA), and 0.5 gram microcrystaline cellulose (Avicel™ HP101, FMC, USA) were added and well mixed to produce a homogeneous mass in an appropriate consistency for passing through a granulating net.

C) Obtained wet mass was granulated and dried in an oven or microwave oven as described in example 1.

*Artemisia abrotantum* granules, prepared according to the present example, were devoid of the original bitter taste and after taste. Resulting granules of *Artemisia abrotantum* are useful against digestive parasites and are appropriate for use in gastrointestinal disorders that are traditionally treated with *Artemisia abrotantum*.

Example 5

*Gingko Biloba* and Concentrated Soy Proteins

*Gingko biloba* pure concentrated extracts are typical bitters. *Gingko biloba* (Frutarom Meer, Haifa, Israel) is standardized concentrated 24% gingkolides bitter powder, characterized by the large fraction of many water insoluble ingredients.
- A) 0.1 of soybean lecithin was mixed and swelled in 1 ml of water at room temperature.
- B) 0.5 a gram of *Gingko biloba* was added and well mixed to obtain a homogeneous liquid paste.
- C) Five grams of functional soy proteins (Solcon™ HV, Solbar Ashdod, Israel) were added and well mixed with QS of water to produce a homogeneous mass in an appropriate consistency ready for passing through a granulating net.
- D) The obtained wet mass was granulated and dried in an oven or microwave oven as described in example 1.

Three aliquots of equivalent to ten mg of *Gingko biloba* powder in 10 ml water were prepared and their bitterness evaluated:
- 1) *Gingko biloba* powder in water was typically bitter and very unpleasant in the mouth.
- 2) *Gingko biloba* in water, mixed with lecithin and Solcon™ HV, was equally as bitter; and
- 3) *Gingko biloba* granules, prepared according to the present example, were devoid of the original bitter taste and contained no after taste at all.

The granules were tested to have less then 5 percent bound water as measured as "loss on dry" by placing a sample of the granules or solid matrix in a weighing oven at 110° C. and calculating the lost weight after one hour.

Example 6

*Gingko Biloba* and Isolated Soy Proteins

- A) 1 gram of soybean lecithin was mixed and swelled in 8 ml of water at room temperature.
- B) 1 gram of *Gingko biloba*, standardized 24% Gingcolides, (Frutarom Meer, Haifa, Israel) was added and well mixed to obtain a homogeneous liquid paste.
- C) 2.5 grams of functional isolated soy proteins (Supro™ 810, Protein Technology International, St Louis, Mo., USA) were added and well mixed to produce a homogeneous mass or dough, in an appropriate consistency ready for passing through a granulating net.
- D) The obtained wet mass was granulated and dried in a microwave oven as described in example 1.

Three aliquots of equivalent to ten mg of *Gingko biloba* powder in 10 ml water were prepared and their bitterness evaluated:
- 1) *Gingko biloba* powder in water was typically bitter and very unpleasant in the mouth.
- 2) *Gingko biloba* in water, mixed with lecithin and Solcon™ HV, was equally as bitter; and
- 3) *Gingko biloba* granules, prepared according to the present example, was devoid of the original bitter taste and contained no after taste at all.

The granules were tested to have less then 5 percent bound water as measured as "loss on dry" by placing a sample of the granules or solid matrix in a weighing oven at 110° C. and calculating the lost weight after one hour.

Example 7

*Gingko Biloba* Instant Powder

The obtained granules of example 6 were ground to homogeneity with instant fruit flavored powders. The resulting powder is reconstituted with tap water to produce in-situ a tasteful beverage. The desired dose of *Gingko Biloba* extract is delivered in a glass of beverage, which is preferred by those who experience difficulties when swallowing tablets or capsules.

Example 8

*Gingko Biloba* Bars

Resulting granules of example 6 were mixed with granola and honey or isomaltose premix to produce a regular, a low calorie, or a diabetic bar delivering doses of *Gingko biloba* extracts without the unwanted bitter taste associated with *Gingko biloba* extracts.

Example 9

Saw Palmetto

Saw palmetto 90% fatty sterol and lipid (frutarom meer, Haifa, Israel) is a water insoluble, oily substance that does not mix with water.
- A) 0.5 grams of soybean lecithin was mixed and swelled in 3 ml of water at room temperature.
- B) 0.5 grams of Saw palmetto fatty sterols (90%) was added and well mixed to obtain a homogeneous liquid paste.
- C) 1.0 gram of concentrated soy protein (Solcon™ HV, Solbar, Ashdod, Israel) was added and well mixed with QS of water to produce a homogeneous mass in an appropriate consistency ready for passing through a granulating net.
- D) The obtained wet mass was granulated and dried in an oven or microwave oven as described in example 1.

Saw palmetto fatty sterols (90%) were mixed in water with lecithin or with functional soybean protein, or both, to yield a non-homogeneous dispersion which, after the high energy emulsification step, could be further homogenized to yield emulsion or related dispersion systems. Saw palmetto, dry powder 25% fatty sterols, (Frutarom Meer) obtained by spray drying Saw palmetto fatty sterols (90%) with filler excipients such as dextrins, were mixed in water and resulted in a separation of the lipids which floated on top of the water within a short period of time. Obtained granules, whilst dispersed in water, did not release Saw palmetto fatty sterols (90%) and no lipid was floating even after many weeks.

Example 10

Coenzyme Q10 and Concentrated Soy Proteins

Ubiquinone is a very hydrophobic water insoluble and lipid soluble solid substance. Ubiquinone was obtained as a solid crystal powder.

A) 0.5 grams of soybean lecithin was mixed and swelled in 3 ml of water at room temperature.
B) 0.5 grams of Ubiquinone was added and mixed well, to obtain a homogeneous liquid paste.
C) 1.0 gram of concentrated soy proteins (Solcon™ HV, Solbar, Ashdod, Israel) was added and mixed well with QS of water to produce a homogeneous mass in a consistency ready for passing through a granulating net.
D) An obtained wet mass was granulated and dried in an oven or microwave oven as described in example 1.

Ubiquinone was mixed in water with lecithin, functional soybean protein or both, which resulted in a very limited yield of non-homogeneous dispersion. A large part of the Ubiquinone was still in crystal particles. The Ubiquinone was dispersed uniformly in the homogeneous amorphous matrix. The granules dispersed well in water and did not release the Ubiquinone, and no lipid was floating after many weeks. The granules were tested to have less then 7 percent bound water as measured as "loss on dry" by placing a sample of the granules or solid matrix in a weighing oven at 110° C. and calculating the lost weight after one hour.

Example 11

Ubiquinone, Coenzyme Q10 and Isolated Soy Proteins

A) 0.5 grams of soybean lecithin was mixed and swelled in 3 ml of water at room temperature.
B) 0.5 grams of Ubiquinone was added and mixed well, to obtain a homogeneous liquid paste.
C) 1.0 gram of isolated soy proteins (Supro™ 810, Protein Technologies International, USA) was added and mixed well with QS of water to produce a homogeneous mass in consistency ready for passing through a granulating net.
D) An obtained wet mass was granulated and dried in a microwave oven, initial burst heat of 110° C. or short high energy in a microwave oven to ensure protein denaturing and continuous drying at lower temperature to avoid Ubiquinone degradation.

The Ubiquinone was dispersed uniformly in the homogeneous amorphous matrix.

Example 12

Ubiquinone, Coenzyme Q10 and Isolated Soy Proteins

A) 0.5 grams of soybean lecithin was mixed and swelled in 3 ml of water at room temperature.
B) 0.5 grams of Ubiquinone was added and mixed well, to obtain a homogeneous liquid paste.
C) 1.0 gram of isolated soy proteins (Supro™ 810, Protein Technologies International, USA) and 1.0 gram of microcrystaline cellulose (Avicel PH101, FMC, USA) were added and mixed well with QS of water to produce a homogeneous mass in consistency ready for passing through a granulating net.
D) An obtained wet mass was granulated and dried in a microwave oven as in example 11 above.

The Ubiquinone was dispersed uniformly in the homogeneous amorphous matrix.

Example 13

Ubiquinone, Coenzyme Q10 and Isolated Soy Proteins

A) 0.5 grams of soybean lecithin was mixed and swelled in 3 ml of water at room temperature.
B) 0.5 grams of Ubiquinone was added and mixed well, to obtain a homogeneous liquid paste.
C) 1.0 gram of isolated soy proteins (Supro™ 810, Protein Technologies International, USA) and 0.5 gram of microcrystaline cellulose (Avicel PH101, FMC, USA) and 0.5 gram of fumed silica (Tixosil, Rhone-Poulenc, France) were added and mixed well with QS of water to produce a homogeneous mass in consistency ready for passing through a granulating net.
D) An obtained wet mass was granulated and dried in a microwave oven.

The Ubiquinone was dispersed uniformly in the homogeneous amorphous matrix. Ubiquinone granules of examples 10, 11, 12 and 13 show at least 98 percent of weighted dose as non-degraded, as detected by an HPLC assay.

Example 14

Vitamin E

Vitamin E, Tocopherol acetate is a water-insoluble, oily substance that does not dissolve in water.
A) 0.5 grams of soybean lecithin was mixed and swelled in 5 ml of water at room temperature.
B) 0.5 grams of Vitamin E was added and mixed well to obtain a homogeneous liquid paste.
C) 1.0 grams of functional soy proteins (Supro™ 810, Protein Technologies International, USA), or wheat proteins (10.0 grams of Prolite™ ADM, USA) was added and equally mixed with QS of water to produce a homogeneous mass in a desired consistency ready for passing through a granulating net.
D) An obtained wet mass was granulated and dried in an oven or microwave oven.

A homogeneous dispersion of Vitamin E was obtained in the granule matrix. Obtained granules dispersed in water did not release the Vitamin E and, consequently, no Vitamin E was floating after at least one month.

Example 15

Lycopene

Lycopene is a water-insoluble, oily substance that does not mix or dissolve in water.
A) 0.5 grams of soybean lecithin was mixed and swelled in 1 ml of water at room temperature.
B) 0.5 grams of 10% Lycopene in tomato oleoresins, Lycomato, (Lycored, Beer-Sheva, Israel), was added and equally mixed to obtain a homogeneous liquid paste.
C) One gram of functional soy proteins (Solcon™ HV), Solbar hatsor or wheat proteins (10.0 grams of Prolite™ ADM, USA), were added and mixed with QS of water to produce a homogeneous mass in a desired consistency for passing through a granulating net.
D) An obtained wet mass was granulated and dried in an oven or microwave oven.

Lycopene was mixed in water with lecithin; functional soybean protein or both to yield a non-homogeneous dispersion that, after the high energy emulsification step, could be further homogenized to yield emulsion or related dispersion systems. A homogeneous dispersion of Vitamin E was obtained in the granule matrix. Obtained granules dispersed in water did not release Lycopene, and no Lycopene was floating after many weeks.

The granules were tested to have less then 4 percent bound water as measured as "loss on dry" by placing a sample of the granules or solid matrix in a weighing oven at 110° C. and calculating the lost weight after one hour.

Example 16

Ubiquinone, Coenzyme Q10 and Isolated Soy Proteins

A) 0.5 grams of soybean lecithin was mixed and swelled in 3 ml of water at room temperature.
B) 0.5 grams of Ubiquinone was added and mixed well, to obtain a homogeneous liquid paste.
C) 4.0 gram of isolated soy proteins (Supro™ 810, Protein Technologies International, USA) was added and mixed well with QS of water to produce a homogeneous mass in a consistency ready for passing through a granulating net.
D) An obtained wet mass was granulated and dried in a microwave oven.

The Ubiquinone was found to be uniformly dispersed in the homogeneous amorphous matrix.

Example 17

*Aloe Vera* S.D. and Isolated Soy Proteins

A) 0.5 gram of soybean lecithin, (Phospholipon 90, Natterman, Germany) was mixed and swelled in 4 ml of water at room temperature.
B) 0.5 gram of *Aloe Vera* S.D. dry extract (Frutarom Meer) was added and well mixed to obtain a homogeneous fluid paste.
C) 5.0 gram of functional soy proteins isolate (Supro™ EX34K, Protein Technologies International, USA), were added and mixed well with QS of water to produce a homogeneous mass in the appropriate consistency for passing through a granulating net.
D) An obtained wet mass was mesh granulated and dried in ovens or microwave ovens.

*Aloe Vera* S.D. soy protein granules, suspended in water were devoid of the original bitter unpleasant taste and after taste.

Example 18

*Gingko Biloba* and Isolated Soy Proteins

A) 1 gram of soybean lecithin was mixed and swelled in 10 ml of water at room temperature.
B) 1 gram of Gingko biloba, standardized 24% Gingcolides, (Frutarom, Meer, Israel) was added and well mixed to obtain a homogeneous liquid paste.
C) 10 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The Obtained wet mass was granulated and dried in a microwave oven.

Three aliquots of equivalent to a dose of fifty mg of *Gingko biloba* powder in 100 ml tomato juice were prepared and their bitterness evaluated: *Gingko biloba* powder in tomato juice was typically bitter and very unpleasant in the mouth. *Gingko biloba* mixed with lecithin and Solcon™ HV, was equally as bitter. *Gingko biloba* granules, prepared according to the invention, were devoid of the original bitter taste and contained no after taste at all for several hours. The granules were tested to have less then 7 percent bound water as measured as "loss on dry" by placing a sample of the granules or solid matrix in a weighing oven at 110° C. and calculating the lost weight after one hour.

Example 19

Fish Oil and Isolated Soy Proteins

A) 0.5 gram of soybean lecithin was mixed and swelled in 4 ml of water at room temperature.
B) 2.5 gram of Fish oil, (Denofa, Norway) was added and well mixed to obtain a homogeneous liquid paste.
C) 5.5 grams of functional isolated soy proteins (Supro™ 810, Protein Technology International, St Louis, Mo., USA) or wheat proteins (Prolite™ ADM, USA) and 1.5 grams fumed silica (Aerosil 200) were added and well mixed to produce a homogeneous mass or dough, in an appropriate consistency ready for passing through a granulating net.
D) The obtained wet mass was granulated and dried.

Up to one gram of carbohydrates such as maltodextrins (Fibersol™, ADM, USA) or carob dry powder replacing the protein were prepared in order to control granule hardness and crunchiness.

The unpleasant typical fish oil taste and texture in the mouth were masked by replacing part of the proteins with Aerosil 200 (Degussa, Germany), which increases the flow property of the granules, and dramatically decreases oxidation, thus resulting in the masking of the unpleasant smell.

Granules stored in airtight glass vials or aluminum foil under nitrogen was devoid of the typical oxidation smell for up to three years at room temperature.

Example 20

Ferrous Sulfate and Isolated Soy Proteins

A) 1 gram of soybean lecithin was mixed and swelled in 8-10 ml of water at room temperature.
B) 1 gram of ferrous sulfate was added and well mixed.
C) 20 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The obtained wet mass was granulated and dried.

Three aliquots of equivalent to a dose of 10 mg of ferrous sulfate in 100 ml tomato juice were prepared and their bitterness evaluated: ferrous sulfate was typically bitter and very unpleasant in the mouth. Ferrous sulfate mixed with lecithin and Solcon™ HV, was equally as bitter while ferrous sulfate granules, prepared according to the invention, were devoid of the original bitter taste and contained no after taste at all for several hours. The granules were tested to have less then 4 percent bound water as measured as "loss on dry" by placing a sample of the granules or solid matrix in a weighing oven at 110° C. and calculating the lost weight after one hour.

Example 21

Ferrous Chelate and Isolated Soy Proteins

A) 1 gram of soybean lecithin was mixed and swelled in 8-10 ml of water at room temperature.
B) 1 gram of ferrous chelate (ferrous glycinate or ferrous protein hydrolysate) was added and well mixed.
C) 40 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The obtained wet mass was granulated and dried.

Three aliquots of equivalent to a dose of 10 mg of ferrous chelate in 100 ml tomato juice were prepared and their bitterness evaluated: Ferrous sulfate was typically bitter and very unpleasant in the mouth. Ferrous sulfate mixed with lecithin and Solcon™ HV, was equally as bitter while ferrous chelate granules, prepared according to the invention, were devoid of the original bitter taste and contained no after taste at all for several hours. The granules were tested to have less then 3 percent bound water as measured as "loss on dry" by placing a sample of the granules or solid matrix in a weighing oven at 110° C. and calculating the lost weight after one hour.

Example 22

Melatonin and Isolated Soy Proteins

A) 1 gram of soybean lecithin was mixed and swelled in 10 ml of water at room temperature.
B) 1 gram of Melatonin was added and well mixed to obtain a homogeneous liquid paste.
C) 40 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The obtained wet mass was granulated and dried.

The typical unpleasant taste of Melatonine was well masked in the granules. The granules were tested to have less then 7 percent bound water as measured as "loss on dry" by placing a sample of the granules or solid matrix in a weighing oven at 110° C. and calculating the lost weight after one hour.

Example 23

Isoflavones and Isolated Soy Proteins

A) 1 gram of soybean lecithin was mixed and swelled in 10 ml of water at room temperature.
B) 1 gram of Isoflavones (Solgen 10 or Solgen 40, Solbar plant extracts, Ashdod, Israel) was added and well mixed to obtain a homogeneous liquid paste.
C) 8 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The obtained wet mass was granulated and dried.

Three aliquots of samples equivalent to 30 mg of Isoflavones in 100 ml yogurt or tomato juice were prepared and their bitterness evaluated: Solgen-10 powder typically has a bitter and unpleasant aftertaste in the mouth. Solgen-10 mixed with lecithin and Solcon™ HV, was equally as bitter while Isoflavones granules, prepared according to the invention, were devoid of the original unpleasant taste and contained no aftertaste at all, even after being refrigerated for several weeks.

The temperature profile of air and product during a lab scale fluidized bed denaturing and drying process of one Kg Isoflavones granules performed according to example 23 is presented in FIG. 1. The operation temperature of the hot air was started at 120° C., and the heating function was stopped while the blower continued until the temperature was equilibrated at 80° C.

Example 24

Isoflavones and Isolated Soy Proteins

A) 1 gram of soybean lecithin was mixed and swelled in 10 ml of water at room temperature.
B) 6 gram of Isoflavones (Nutragen-3, Solbar plant extracts, Ashdod, Israel) was added and well mixed to obtain a homogeneous liquid paste.
C) 3 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The obtained wet mass was granulated and dried.

Example 25

Isoflavones and Isolated Soy Proteins

A) 1 gram of soybean lecithin was mixed and swelled in 10 ml of water at room temperature.
B) 6 gram of Isoflavones (Soylife25, Soylife, Netherland) was added and well mixed to obtain a homogeneous liquid paste.
C) 3 grams of functional isolated soy proteins (Supro™ 810, Protein Technology International, St Louis, Mo., USA) were added and well mixed to produce a homogeneous mass or dough, in an appropriate consistency ready for passing through a granulating net.
D) The obtained wet mass was granulated and dried in a microwave oven.

Example 26

Zinc Gluconate and Carob Granules

A) 1 gram of soybean lecithin was mixed and swelled in 8-10 ml of water at room temperature.
B) 1 gram of Zinc gluconate was added and well mixed.
C) 35 grams of functional isolated soy proteins (Supro™ 810, Protein Technology International, St Louis, Mo., USA) or wheat proteins (Prolite™ ADM, USA) and 5 grams of dry Carob powder (Carbohydrates) were added and well mixed to produce a homogeneous mass or dough, in an appropriate consistency ready for passing through a granulating net.
D) The obtained wet mass was granulated and dried.

Zinc gluconate is typically bitter, and causes a metallic sensation and very unpleasant taste in the mouth. Zinc gluconate mixed with lecithin and isolated soy proteins, was equally as bitter while Zinc gluconate granules, prepared according to the invention, was devoid of the original bitter taste and contained no metallic after taste at all for several hours.

The temperature profile of air and product during a lab scale fluidized bed denaturing and drying process performed on one Kg Zinc gluconate granules according to example 26, is presented in FIG. 1. The operation temperature of the hot air started at 160° C. and the heating function was stopped while the blower continued until equilibrated at 80° C.

Example 27

Dispersion of Granules in Water

A) 1 gram of granules of above examples 5, 19, 20 or 26, were placed in 100 ml of tap water at room temperature with slight mixing.
B) The granules were observed after one hour, six hours and twenty hours, and were found to have almost no changes.
C) They were then separated from the water by filter paper, and dried for one hour at 70° C.

The granules were reconstituted and dried and showed no substantial disintegration in water. Weight loss after 24 hours was from 3% to 20% apparently due to the leak of soluble ingredients of the matrix such as the lecithin into the water medium.

TABLE 1

Granules weight following dispersion in water

| Granules of example number | Weight at beginning of test | Weight following test, 24 hours in water at room temperature |
| --- | --- | --- |
| Gingko - example 5 | 1.00 grams | 0.75 grams |
| Ferrous - example 20 | 1.00 grams | 0.82 grams |
| Fish oil - example 19 | 1.00 grams | 0.88 grams |
| Zinc gluconate - example 26 | 1.00 grams | 0.92 grams |

Example 28

Dispersion of Granules in Simulated Gastric Fluids Followed by Intestinal Fluids Simulated gastric fluids (SGF) with pH 1.5 and Simulated intestinal fluids (SIF) with a pH of 7.4 and with pancreatic enzymes, (dry and calibrated concentrate porcine pancreatic extract, purchased from Sigma, Israel) were prepared according to USP. 1 gram of granules was dispersed in 100 ml of SGF for 30 minutes and transferred to SIF, all at 35 □C under mild mixing, 100 RPM with a magnetic stirrer. Granules were reconstituted by separation on filter paper and dried and weighed at specific time points as summarized in table 2.

TABLE 2

Granule weight after dispersion in SGF followed by SIF

| Conditions/Granules | Reconstituted weight of example 5 granules | Reconstituted weight of example 26 granules |
| --- | --- | --- |
| Start | 1.00 grams | 1.00 grams |
| 30 minutes SGF | 0.88 grams | 0.95 grams |
| 20 minutes SIF (50 min total) | 0.45 grams | 0.65 grams |

TABLE 2-continued

Granule weight after dispersion in SGF followed by SIF

| Conditions/Granules | Reconstituted weight of example 5 granules | Reconstituted weight of example 26 granules |
| --- | --- | --- |
| 40 minutes SIF (70 min total) | 0.25 grams | 0.55 grams |
| 120 minutes SIF (150 min total) | 0.10 grams | 0.25 grams |

The granules were intact and did not swelled or changed size or disintegrate in 30 minutes in the SGF. In contrast, the granules disintegrated: lost integrity swelled and become very soft mass with two to five folds in size until complete disintegration within less than four hours in the SIF.

Example 29

Lutein Esters Granules

A) 1 gram of soybean lecithin, Epikuron K100, was mixed and swelled in 5 ml of water at room temperature for 15 minutes.
B) 1 gram of Lutein ester was added and well mixed until homogeneous dispersion was obtained.
C) 4 grams of functional isolated soy proteins (I 700, China) were added and mixed thoroughly to produce a homogeneous mass or dough, in an appropriate consistency ready for passing through a granulating net.
D) The obtained wet mass was granulated and heated in a microwave oven for 60 seconds on maximum microwave strength and protein denaturating was observed visually as granules were changing shape and hardened.
E) Drying was performed by air blow oven at 70 □C for 40 minutes, and granule weight was monitored every ten minutes until no water loss was measured between two consecutive weights.

Example 30

Lutein Granules of Various Hardness

A) 1.0 grams of Soybean lecithin, Epikuron™ K100, was mixed and swelled in 5 ml of water at room temperature for 15 minutes.
B) 1.0 grams Lutein was added and well mixed until homogeneous dispersion was obtained.
C) 8.0 grams Isolated soy proteins (I 700, China) were added with or without increasing the amount of dry Carob powder and mixed thoroughly to produce a homogeneous mass or dough, in an appropriate consistency ready for passing through a granulating net.
D) The obtained wet mass was granulated and heated in a microwave oven for 60 seconds on maximum microwave strength and protein denaturating was observed visually as granules changed shape and hardened.
E) Drying was performed by air blow oven at 70 □C for 40 minutes, and granule weight was monitored every ten minutes until no water loss was measured between two consecutive weights.

The hardness of the granules increased as a direct function of increased Carob content; less hard granules were produced without Carob content, harder granules were produced with 1.0 grams of Carob and granules with the highest hardness were produced with 2.0 grams of Carob incorporated in the matrix.

TABLE 3

| Lutein matrix | | | |
|---|---|---|---|
| Compositions | W/W % | W/W % | W/W % |
| Lutein | 10 | 10 | 10 |
| Epikuron K100 | 10 | 10 | 10 |
| Isolated soy protein (I700) | 80 | 70 | 60 |
| Carob dry powder | 00 | 10 | 20 |
| Hardness | lowest | Medium | Highest |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

All publications, patents, and patent applications cited herein are hereby incorporated by reference in their entirety for all purposes.

What is claimed is:

1. A homogeneous, granular, solid matrix composition that is substantially insoluble in aqueous medium, and substantially insoluble for at least two hours in gastric juices, and which solid matrix completely disintegrates in the presence of digestive proteolytic enzymes or intestinal juices, said solid matrix comprising: a) at least 10% w/w vegetable proteins; b) lecithin; c) and at least one ingestible bioactive compound, which compound is at least partially insoluble in an aqueous medium and is dispersed or solubilized in said granular solid matrix.

2. A composition of claim 1, wherein said solid granules do not disintegrate or substantially loose their shape within two hours in simulated gastric fluids, and wherein said solid matrix substantially disintegrates within six hours in simulated intestinal fluids comprising pancreatic enzymes.

3. A composition of claim 1, wherein said bioactive agent is at least partially insoluble in an aqueous medium and is embedded in a substantially molecular or uniform non-crystalline dispersion.

4. A composition of claim 1, wherein the ratio of vegetable protein to the combined amounts of lecithin and ingestible bioactive compound is between about 40:1 and 1:4.

5. A composition of claim 1, wherein the ratio of vegetable protein to the combined amounts of lecithin and ingestible bioactive compound is between about 10:1 and 1:1.

6. A composition of claim 1, wherein said ingestible bioactive compound has a water solubility of less than 10 mg/ml at 25° C.

7. A composition of claim 1, wherein said vegetable proteins are concentrated and isolated proteins selected from the group consisting of: corn, potatoes, wheat, peanuts, beans, rice, sesame, barley, sunflower, canola and rapeseed.

8. A composition of claim 1, wherein said ingestible bioactive compound is selected from the group consisting of: a drug, a nutrient, a vitamin, a food supplement, an enzyme, a coenzyme, an oil, omega 3, omega 6, lutein, lycopene or their esters, and mixtures thereof.

9. A method of use of the solid matrix according to claim 1, wherein said solid matrix is in the shape of granules that are filled into capsules; pressed in tablets; are dispensed in sachets; and admixtured with semi-solid food, solid foods, premixed, or mixed in-situ, in order to form compositions for the administration thereof.

10. A process of preparing a homogeneous, granular, solid matrix composition that is substantially insoluble in aqueous medium, and substantially insoluble for at least two hours in gastric juices, and which solid matrix completely disintegrates in the presence of digestive proteolytic enzymes or intestinal juices, said composition comprising at least one bioactive ingestible which is at least partially insoluble in an aqueous medium, wherein said at least one bioactive ingestible is embedded in a substantially molecular or uniform non-crystalline dispersion by the aid of lecithin in a matrix made of at least 10% vegetable proteins which are denatured in said granules, said process comprising the steps of:
 a. dispersing or solubilizing said at least one bioactive ingestible in a lecithin-water mixture to form a dispersion, wherein said at least one bioactive ingestible is at least partially water insoluble in an aqueous medium;
 b. mixing non-denatured vegetable proteins with the dispersion of step (a) to obtain a wet mass;
 c. granulating said wet mass; and
 d. heat treating the wet granules to above at least 70° C. to denature said non-denatured vegetable protein and to obtain solid dry granules with said at least one bioactive ingestible incorporated therein.

11. A process of claim 10, wherein the denaturing heat is applied for less then 10 minutes and most preferable for less then 5 minutes.

12. A process of claim 10, whereas the denaturing heat is applied for less then 2 minutes and most preferable for less then 1 minute.

13. A process of claim 10, wherein the ratio of vegetable protein to the combined amounts of lecithin and ingestible bioactive compound is between about 40:1 and 1:4.

14. A process of claim 10, wherein the ratio of vegetable protein to the combined amounts of lecithin and ingestible bioactive compound is between about 10:1 and 1:1.

15. A process of claim 10, wherein said ingestible bioactive compound has a water solubility of less than 10 mg/ml at 25° C.

16. A process of claim 10, wherein said vegetable proteins are concentrated and isolated proteins selected from the group consisting of: corn, potatoes, wheat, peanuts, beans, rice, sesame, barley, sunflower, canola and rapeseed.

17. A process of claim 10, wherein said ingestible bioactive compound is selected from the group consisting of a drug, a nutrient, a vitamin, a food supplement, an enzyme, a coenzyme, an oil, omega 3, omega 6, lutein, lycopene or their esters and mixtures thereof.

18. A process of claim 10, wherein the granules are free flowing and filled into capsules or pressed in tablets.

19. A composition for releasing bioactive ingestibles, locally in the intestine, whenever prepared according to the process of claim 10, said composition comprising bioactive ingestibles that are at least partially insoluble in an aqueous medium, wherein said composition is made of a homogeneous dispersion of said bioactive ingestibles in a homoge neous solid matrix comprising lecithin and vegetable proteins, wherein said vegetable proteins are isolated and concentrated vegetable proteins containing at least 40% w/w proteins and said proteins are denatured in said homogeneous solid matrix, and wherein said proteins are at least partially non-denatured before the drying process and are thereafter denatured in said homogeneous solid matrix.

20. A method of use of the granules produced according to the process of claim 10, wherein the granules are filled into capsules, pressed in tablets, are dispensed in sachets, admixtured with semi-solid food, solid foods, premixed, or mixed in-situ in order to form compositions for the administration thereof.

* * * * *